Figure 1:
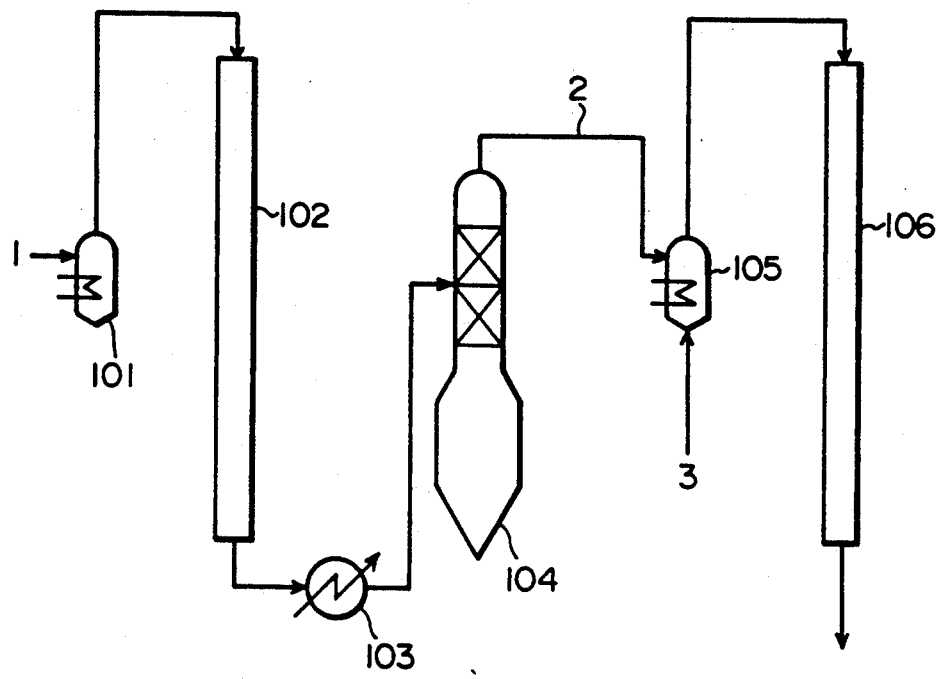

United States Patent [19]

Shimasaki et al.

[11] Patent Number: 5,235,107
[45] Date of Patent: Aug. 10, 1993

[54] METHOD OF PRODUCING ETHYLENEDIAMINES

[75] Inventors: Yuuji Shimasaki, Takatsuki; Hideaki Tsuneki, Tokyo; Youichi Hino, Sakai; Tetsuro Hayashi, Takatsuki; Michio Ueshima, Takarazuka, all of Japan

[73] Assignee: Nippon Shokubai Kagaku Kogyo Co., Ltd., Osaka, Japan

[21] Appl. No.: 683,498

[22] Filed: Apr. 10, 1991

Related U.S. Application Data

[63] Continuation of Ser. No. 440,302, Nov. 22, 1989, abandoned.

[30] Foreign Application Priority Data

Nov. 22, 1988 [JP] Japan .................. 63-293664
Dec. 1, 1988 [JP] Japan .................. 63-302218

[51] Int. Cl.$^5$ .......................... C07C 209/62
[52] U.S. Cl. .................................. 564/487
[58] Field of Search .......................... 564/487

[56] References Cited

U.S. PATENT DOCUMENTS

| | | | |
|---|---|---|---|
| 2,318,730 | 5/1943 | Wilson | 260/583 |
| 3,215,742 | 11/1965 | Harlenko et al. | 260/585 |
| 3,527,757 | 9/1970 | Austin et al. | 260/247.5 |
| 3,555,941 | 2/1971 | Dick et al. | 260/465.5 |
| 4,436,891 | 3/1984 | Umeda et al. | 564/487 |
| 4,578,517 | 3/1986 | Johnson et al. | 564/479 |
| 4,740,620 | 4/1988 | Dixon et al. | 564/409 |

FOREIGN PATENT DOCUMENTS

| | | | |
|---|---|---|---|
| 0703735 | 2/1965 | Canada . | |
| 1037126 | 8/1958 | Fed. Rep. of Germany | 564/487 |
| 58-46041 | 3/1983 | Japan . | |
| 58-46042 | 3/1983 | Japan . | |
| 3122652 | 5/1988 | Japan . | |

OTHER PUBLICATIONS

Grant, ed. *Hackh's Chem. Dict.*, 4th Ed., McGraw-Hill Book Co., (1969) New York, pp. 437-438.
Chemical Abstracts, vol. 109, No. 25, Dec. 19, 1988;
The Journal of the American Chemical Society, vol. LXX, Jan.-Mar., 1948.

Primary Examiner—Richard L. Raymond
Assistant Examiner—Peter G. O'Sullivan
Attorney, Agent, or Firm—Sherman and Shalloway

[57] ABSTRACT

A method of producing ethylenediamines represented by the general formula $$H_2NCH_2CHNH_2 \atop R \qquad (I)$$

wherein R represents a hydrogen atom, or a methyl or ethyl group, which comprises reacting an aziridine compound of the general formula $$\underset{H}{\underset{\diagdown \;\; \diagup}{\underset{N}{CH_2\text{———}CH\text{—}R}}} \qquad (II)$$

wherein R is as defined, with ammonia in the gaseous phase in the presence of a solid acid catalyst. In another aspect, a method of producing ethylenediamines f the general formula (I), which comprises reacting a reaction product containing an aziridine compound of the general formula (II), obtained by the gaseous phase intramolecular dehydration reaction of an alkanolamine represented by the general formula $$\underset{X \;\;\;\; Y}{CH_2\text{—}CH\text{—}R} \qquad (III)$$

wherein X represents the OH group or the NH$_2$ group, Y represents the NH$_2$ group when X is the OH group and the OH group when X is the NH$_2$ group, and R is as defined, in the presence of a catalyst A, with ammonia in the gaseous phase in the presence of a solid acid catalyst (catalyst B).

10 Claims, 1 Drawing Sheet

METHOD OF PRODUCING ETHYLENEDIAMINES

This application is a continuation of application Ser. No. 07/440,302, filed Nov. 22, 1989, now abandoned.

Ethylenediamines, that is, ethylenediamine and its derivatives, find extensive use in many fields including the textile industry and the rubber industry, and also as agricultural chemicals and medicines.

A method comprising reacting ethylene dichloride with ammonia under high pressures (EDC method) is known as a technique of industrially producing ethylenediamine. In this method, the conversion of ethylene dichloride is almost quantitative, but the resulting ethylenediamine further reacts with ethylene dichloride to form ethylenamines such as diethylenetriamine and triethylenepentamine as by-products. Hence, this method should properly be said to be a method of producing ethylenamines as well rather than a method of producing ethylenediamine alone. Furthermore, this method has the disadvantage that by-product inorganic salts and vinyl chloride monomer must be discarded, and that because of the need for additional equipment for disposing of these compounds and the corrosion of the reaction apparatus by a chlorine ion, the cost of the entire equipment becomes high.

A method of producing ethylenediamine by reductive amination of monoethanolamine is also known. This method involves reacting monoethanolamine with ammonia in the presence of hydrogen using a nickel- or cobalt-containing catalyst. This reaction does not produce ethylenediamine alone, but forms ethylenamines as well. Furthermore, this method has the disadvantage that the conversion of monoethanolamine is low, alcoholic hydroxyl-containing by-products such as cyclic amines or aminoethylethanolamine form, and that the reaction requires pressures as high as several tens of $kg/cm^2$ to one hundred and several tens of $kg/cm^2$.

Recently, a method (MEA method) starting from monoethanolamine but not going through reductive amination was disclosed in some patent documents (Japanese Laid-Open Patent Publications Nos. 236752/1986, 18324/1986 and 94944/1985). This method involves a batch reaction in the liquid phase and requires high reaction pressures, and the selectivity for ethylenediamine is not sufficient.

A reaction in a flow system was also disclosed (European Patent No. 252424). This method requires a high reaction pressure of at least about 10 $kg/cm^2$, and yet the selectivity for ethylenediamine is at most 60% by weight and cyclized products of aminoethylethanolamine are formed as by-products in an amount of 20 to 40% by weight.

It is an object of this invention to solve the above problems of conventional methods of producing ethylenediamines, and to provide a method of producing ethylenediamines at a high selectivity by a gaseous phase reaction without involving the problems of the formation of by-products such as inorganic salts and vinyl chloride monomer and the corrosion of the equipment as in the EDC method, and without requiring high pressures as in the MEA method.

We have now found that ethylenediamines can be produced with a very high conversion and selectivity by a novel reaction of aziridine compounds with ammonia in the gaseous phase in the presence of a solid acid catalyst.

Thus, the present invention provides a method of producing ethylenediamines represented by the general formula

 (I)

wherein R represents a hydrogen atom, or a methyl or ethyl group, which comprises reacting an aziridine compound of the general formula

 (II)

wherein R is as defined, with ammonia in the gaseous phase in the presence of a solid acid catalyst.

The aziridine compounds of formula (II) used in this invention are specifically ethylenimine, propylenimine and 2-ethylethylenimine, and they are converted to the corresponding ethylenediamines of formula (I), i.e. ethylenediamine, methylethylenediamine, and ethylethylenediamine.

All types of solid acids may be used as the solid acid catalysts (to be sometimes referred to as catalyst B hereinafter). Examples include oxides such as silicon oxide, zirconium oxide, titanium oxide, aluminum oxide, zinc oxide, cadmium oxide, lead oxide, bismuth oxide, niobium oxide, lanthanum oxide, antimony oxide and yttrium oxide; clay minerals such as kaolin, bentonite and montmorillonite; molecular sieves (including various metal ion exchangers) known as zeolites such as mordenite Y-type zeolite and ZSM-5; and oxo acid salts such as phosphates, borates, sulfates, niobates, tungstates, molybdates and titanates. Among them, the molecular sieves are preferred because they give high conversions and selectivities. These solid acids may be used singly or in combination. The method of preparing catalyst B is not particularly limited, and all methods heretofore practiced generally can be used.

The method of this invention is carried out by passing a starting gas composed of the aziridine compound of formula (II) and ammonia over the solid acid catalyst (catalyst B). The starting gas may, as required, be diluted with an inert gas such as nitrogen or helium.

The mole ratio between ammonia and the aziridine compound in the starting gas affects the selectivity of the ethylenediamine compound formed. If the mole ratio of ammonia to the aziridine compound is low, the amounts of by-product cyclic compounds (piperazines) and by-product polyamines such as diethylenetriamines and triethylenetetramines increase, and the selectivity for the desired ethylenediamine compound is lowered. On the other hand, if the above mole ratio is high, the selectivity for the ethylenediamine compound increases, but the productivity is reduced. Preferably, the mole ratio of ammonia to the aziridine compound in the starting mixture is at least 1, especially from 1 to 50.

The reaction temperature may be properly preset depending upon the types of the aziridine compound, the final product, and/or catalyst B. Preferably, it is 100 to 500° C., especially 200 to 450° C.

The reaction pressure may be atmospheric, reduced or elevated pressure. The space velocity, which varies with the catalyst, the reaction temperature, the reaction materials, etc., is preferably 100 to 30,000 $hr^{-1}$, especially preferably 500 to 10,000 hr$^{-1}$. The reactor used may be of the fixed bed flowing type or the fluidized bed type.

We have also found that ethylenediamines can be produced also by using in the above reaction a product containing aziridine compounds obtained by the gaseous phase intramolecular dehydration reaction of an alkanolamine as a starting material instead of the isolated aziridine compound.

Thus, according to this invention, there is also provided a method of producing ethylenediamines of the general formula $$H_2NCH_2CHNH_2 \atop R \qquad (I)$$

wherein R represents a hydrogen atom, or a methyl or ethyl group, which comprises reacting a reaction product containing an aziridine compound of the general formula

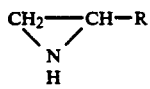 (II)

wherein R is as defined, obtained by the gaseous phase intramolecular dehydration reaction (to be referred to as the first-stage reaction) of an alkanolamine represented by the general formula

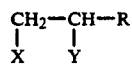 (III)

wherein X represents the OH group or the NH$_2$ group, Y represents the NH$_2$ group when X is the OH group and the OH group when X is the NH$_2$ group, and R is as defined, in the presence of a catalyst (may sometimes be referred to as catalyst A), with ammonia in the gaseous phase in the presence of a solid acid catalyst (catalyst B) (this reaction may be referred to as the second-stage reaction).

Catalyst A in the first-stage reaction may be any catalyst which has the function of converting the alkanolamine into an aziridine compound by the gaseous phase intramolecular dehydration reaction. For example, there can be used the tungsten oxide-type catalyst disclosed in Japanese Patent Publication No. 10593/1975, the catalyst composed of tungsten oxide and silicon disclosed in U.S. Pat. No. 4,301,036, the niobium- or tantalum-containing catalysts disclosed in U. S. Pat. Nos. 4,289,656, 4,337,175 and 4,477,591, the silicon-containing catalyst disclosed in European Laid-Open Patent Publication No. 227,461, and the phosphorus-containing catalysts disclosed in European Laid-Open Patent Publications Nos. 228,898 and 230,776. The following phosphorus containing or silicon-containing catalyst are particularly preferred.

(1) Phosphorus-containing catalysts of the general formula $X_aP_bM_cO_d$ wherein X represents at least one element selected from the group consisting of elements of Group IIIA of the periodic table, silicon, germanium, tin, lead, antimony, bismuth, transition metal elements, lanthanide elements and actinide elements (examples of these elements are B, Al, Tl, Si, Sn, Sb, Bi, Cu, Zn, Cd, Y, Ti, Zr, Nb, Ta, W, Mn, Fe, Ni, La, Ce, Eu and Th), P represents phosphorus, M represents at least one element selected from the group consisting of alkali metal elements and alkaline earth metal elements (examples of these elements are Li, Na, K, Rb, Cs, Sr and Ba), O represents oxygen, when a is 1, b is 0.01 to 6 and c is 0 to 3, and d is a number determined by the values of a, b and c and the states of bonding of the various constituent elements, described in European Laid-Open Patent Publication No. 230,776.

(2) Phosphorus-containing of the general formula $X_aP_bY_cO_d$ wherein X represents at least one element selected from the group consisting of alkali metal elements and alkaline earth metal elements, P represents phosphorus, Y represents at least one element selected from the group consisting of boron, aluminum, silicon, sulfur, titanium, copper, yttrium, zirconium, niobium, tantalum, tungsten, lanthanum and thorium, O represents oxygen, when a is 1, b is 0.05 to 3 and c is 0 to 1, and d is a number determined by the values of a, b and c and the state of bonding of the various constituent elements, disclosed in European Laid-Open Patent Publication No. 228,898.

(3) Silicon-containing catalysts of the general formula $Si_aX_bY_cO_d$ wherein X represents at least one element selected from the group consisting of alkali metal elements and alkaline earth metal elements, Y represents at least one element selected from the group consisting of boron, aluminum, titanium, zirconium, tin, zinc and cerium, O represents oxygen, when a is 1, b is 0.005 to 1, and c is 0 to 1, and d is a number determined by the values of a, b and c, and the state of bonding of the various constituent elements, disclosed in European Laid-Open Patent Publication No. 227,461.

The conditions for the first-stage reaction differ depending upon the catalyst used. Usually, the reaction temperature is 300 to 500° C. The concentration of the alkanolamine in the starting gas is 1 to 100% by volume. The space velocity is 50 to 20,000 hr$^{-1}$. The reaction pressure may be atmospheric, reduced or elevated pressure. The inclusion of an inert gas such as nitrogen, ammonia or the recycled unreacted aziridine compound in the starting gas does not adversely affect the reaction.

The second-stage reaction involves reacting the reaction product of the first-stage reaction with ammonia in the gaseous phase in the presence of catalyst B to produce ethylenediamines.

The catalyst B is as described above.

In the second-stage reaction, the aziridine compound in the product obtained by the first-stage reaction reacts with ammonia in the presence of catalyst B to give ethylenediamine selectively. The conditions for the second-stage reaction have already been described. Preferably, the reaction temperature is 200 to 500° C.; the concentration of the aziridine compound in the starting gas is 1 to 50% by volume; the concentration of ammonia is 1 to 99% by volume; and SV is 100 to 20,000 hr$^{-1}$.

The starting gas to be submitted to the second-stage reaction (the product of the first-stage reaction) may contain an inert gas such as nitrogen and the unreacted alkanolamine or by-products such as water and a small amount of acetaldehyde resulting in the first-stage reaction. After the second-stage reaction, the unreacted ammonia and aziridine compound may be separated from the ethylenediamine product, and reused in the second reaction system.

Both the first-stage reaction and the second-stage reaction may generally be carried out by using a fixed bed-type reactor. If desired, a fluidized bed-type or moving bed-type reactor may be used. The first-stage reaction and the second-stage reaction may be combined as follows:

(a) A reaction tube filled with catalyst A and a reaction tube filled with catalyst B are separately constructed, and the first-stage reaction and the second-stage reaction are carried out independently.

(b) Catalyst A and catalyst B are stacked in one reaction tube so that catalyst A is positioned on its inlet (front) side and catalyst B on its outlet (rear) side. The first-stage reaction is carried out in the inlet side of the reaction tube, and the second-stage reaction is carried out in the outlet side. Preferably, the temperatures of reactions are independently controlled by, for example, providing a partition in a heating bath portion of the reaction tube.

(c) Catalysts A and B are filled in one reaction tube as a mixture or in the alternately stacked state, and the first-stage reaction and the second-stage reaction are carried out in the same reaction tube.

In the case of (a) and (b), the reaction product from the first-stage reaction may be supplemented with ammonia and an aziridine compound, and then submitted to the second-stage reaction. In the case of (a), the reaction product from the first-stage reaction may be submitted to a purification step to purify the aziridine compound and remove the unreacted alkanolamine and the by-product, and introduced as a material for the second-stage reaction.

According to this invention, ethylenediamines can be produced advantageously by the novel gaseous phase reaction. Since this method does not use a starting compound having a halogen atom or an oxygen atom, inorganic salts or chlorine-containing wastes attributed to the starting material do not result as by-products. Furthermore, a high-purity product can be obtained by the method of this invention because hydroxyl group-containing by-products which are difficult to separate from the desired ethylenediamines do not form. Moreover, the method of this invention can be practiced by a gaseous phase flow system, and has excellent productivity.

The following examples illustrate the present invention specifically. In these examples, the conversion of the alkanolamine, the conversion of the aziridine compound, the selectivity for the ethylenediamine, the selectivity for aziridine compound, and the one-pass yield of the ethylenediamine are defined as follows.

$$\text{Conversion of the alkanolamine (mole \%)} = \frac{\text{Moles of the alkanolamine consumed}}{\text{Moles of the alkanolamine fed}} \times 100$$

$$\text{Conversion of the aziridine compound (mole \%)} = \frac{\text{Moles of the aziridine compound consumed}}{\text{Moles of the aziridine compound fed}} \times 100$$

$$\text{Selectivity for the ethylenediamine (mole \%)} = \frac{\text{Moles of the ethylenediamine produced}}{\text{Moles of the alkanolamine consumed or moles of the aziridine compound consumed}} \times 100$$

$$\text{Selectivity for the aziridine compound (mole \%)} = \frac{\text{Moles of the aziridine compound produced}}{\text{Moles of the alkanolamine consumed}} \times 100$$

$$\text{One-pass yield of the ethylenediamine (mole \%)} = \frac{\text{Moles of the ethylenediamine produced}}{\text{Moles of the alkanolamine fed or moles of the aziridine compound fed}} \times 100$$

Figure 2:
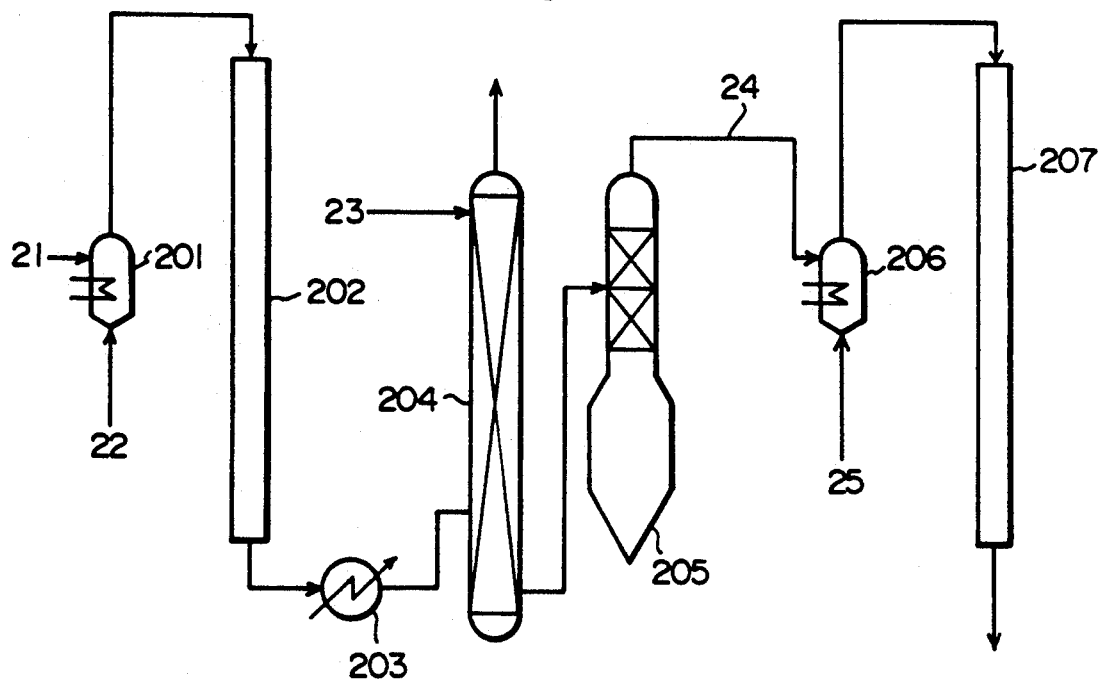

In the accompanying drawings, FIG. 1 is a diagram showing the reaction apparatus used in Example 27, and FIG. 2 is a diagram showing the reaction apparatus used in Example 28.

EXAMPLE 1

Aluminum oxide (granules) were pulverized to a size of 9 to 16 mesh, and calcined in air at 500° C. for 2 hours to obtain catalyst B. Five milliliters of catalyst B was filled in a stainless steel reaction tube having an inside diameter of 10 mm, and then the reaction tube was immersed in a molten salt bath. A starting gas composed of 95% by volume of ammonia and 5% by volume of ethylenimine was passed through the reaction tube at a space velocity of 3,000 hr$^{-1}$ (STP), and reacted. The reaction product was analyzed by gas chromatography, and the results shown in Table 1 were obtained.

EXAMPLE 2

Zirconium oxide (20 g) was kneaded with water, and dried at 120° C. in air, calcined at 500° C. for 2 hours, and pulverized to a size of 9 to 16 mesh to obtain catalyst B. In the presence of catalyst B, a starting gas composed of 95% by volume of ammonia and 5% by volume of propylenimine was passed at a space velocity of 4,000 hr$^{-1}$ (STP) and reacted at a temperature of 380° C. The results are shown in Table 1.

EXAMPLE 3

Niobium pentoxide (20 g) was kneaded with water, dried at 120° C. in air, calcined at 500° C. for 2 hours, and pulverized to a size of 9 to 16 mesh to obtain catalyst B. In the presence of catalyst B, a starting gas composed of 90% by volume of ammonia and 10% by volume of propylenimine was passed at a space velocity of 3,000 hr$^{-1}$ (STP) and reacted at a temperature of 300° C. The results are shown in Table 1.

EXAMPLE 4

Tungstic acid (4.2 g) and 10 g of silicon oxide were kneaded with water, dried at 120° C. in air, calcined at 500° C. for 2 hours, and pulverized to a size of 9 to 16 mesh to obtain catalyst B. In the presence of catalyst B, a starting gas composed of 90% by volume of ammonia and 10% by volume of 2-ethylethylenimine was passed at a space velocity of 3,000 hr$^{-1}$ (STP) and reacted at a temperature of 350° C. The results are shown in Table 1.

EXAMPLE 5

Aluminum phosphate (10 g) was kneaded with water, dried at 120° C. in air, calcined at 500° C. for 2 hours, and pulverized to a size of 9 to 16 mesh to obtain catalyst B. In the presence of catalyst B, a starting gas composed of 80% by volume of ammonia and 20% by volume of ethylenimine was passed at a space velocity of 5,000 hr$^{-1}$ (STP) and reacted at 380° C. The results are shown in Table 1.

EXAMPLE 6

In the presence of the catalyst B prepared in Example 5, a starting gas composed of 10% by volume of ammonia, 10% by volume of ethylenimine and 80% by volume of nitrogen was passed at a space velocity of 4,000 hr$^{-1}$ (STP) and reacted at 370° C. The results are shown in Table 1.

EXAMPLE 7

Boron phosphate (10 g) was kneaded with water, dried in air at 120° C., calcined at 500° C. for 2 hours, and pulverized to a size of 9 to 16 mesh to obtain catalyst B. In the presence of catalyst B, a starting gas composed of 5% by volume of ammonia, 5% by volume of propylenimine and 90% by volume of nitrogen was passed at a space velocity of 4,000 hr$^{-1}$ (STP) and reacted at 350° C. The results are shown in Table 1.

EXAMPLE 8

Potassium hydrogen phosphate (2.27 g) and 10 g of silicon oxide were kneaded with water, dried in air at 120° C., calcined at 500° C. for 2 hours, and pulverized to a size of 9 to 16 mesh to obtain catalyst B. In the presence of catalyst B, a starting gas composed of 80% by volume of ammonia and 20% by volume of ethylenimine was passed at a space velocity of 4,000 hr$^{-1}$ (STP) and reacted at 400° C. The results are shown in Table 1.

EXAMPLE 9

Using the catalyst B prepared in Example 8, a starting gas composed of 50% by volume of ammonia and 50% by volume of ethylenimine was passed at a space velocity of 2,500 hr$^{-1}$ (STP) and reacted at 380° C. The results are shown in Table 1.

EXAMPLE 10

Cesium carbonate (5.43 g), 1.72 g of 95% sulfuric acid and 10 g of silicon oxide were kneaded with water, dried in air at 120° C., calcined at 500° C. for 2 hours, and pulverized to a size of 9 to 16 mesh to obtain catalyst B. In the presence of catalyst B, a starting gas composed of 50% by volume of ammonia, 5% by volume of 2-ethylethylenimine and 45% by volume of nitrogen was passed at a space velocity of 7,000 hr$^{-1}$ (STP) and reacted at 390° C. The results are shown in Table 1.

EXAMPLE 11

Sodium tungstate (5.50 g) and 10 g of silicon oxide were kneaded with water, dried in air at 120° C., calcined at 500° C. for 2 hours, and pulverized to a size of 9 to 16 mesh to obtain catalyst B. In the presence of the catalyst B, a starting gas composed of 50% by volume of ammonia, 5% by volume of propylenimine and 45% by volume of nitrogen was passed at a space velocity of 5,000 hr$^{-1}$ (STP) and reacted at 390° C. The results are shown in Table 1.

EXAMPLE 12

Kaolin (10 g) was kneaded with water, dried in air at 120° C., calcined at 500° C. for 2 hours, and pulverized to a size of 9 to 16 mesh to obtain catalyst B. In the presence of the catalyst B, a starting gas composed of 80% by volume of ammonia and 20% by volume of propylenimine was passed at a space velocity of 6,000 hr$^{-1}$ (STP) and reacted at 400° C. The results are shown in Table 1.

EXAMPLE 13

Using the catalyst B prepared in Example 1, a starting gas composed of 80% by volume of ammonia and 20% by volume of ethylenimine was passed at a space velocity of 500 hr$^{-1}$ (STP) and reacted at 120° C. The results are shown in Table 1.

EXAMPLE 14

Montmorillonite (10 g) was kneaded with water, dried in air at 120° C., calcined at 500° C. for 2 hours, and pulverized to a size of 9 to 16 mesh to obtain catalyst B. In the presence of catalyst B, a starting gas composed of 80% by volume of ammonia and 20% by volume of ethylenimine was passed at a space velocity of 4,000 hr$^{-1}$ (STP) and reacted at 300° C. The results are shown in Table 1.

EXAMPLE 15

ZSM-5 zeolite (10 g) was compression-molded, dried in air at 120° C., calcined at 500° C. for 2 hours and pulverized to a size of 9 to 16 mesh to obtain catalyst B. In the presence of catalyst B, a starting gas composed of 90% by volume of ammonia and 10% by volume of ethylenimine was passed at a space velocity of 9,000 hr$^{-1}$ (STP) and reacted at 430° C. The results are shown in Table 1.

EXAMPLE 16

H mordenite (10 g) was compression-molded, dried in air at 120° C., calcined at 500° C. for 2 hours and pulverized to a size of 9 to 16 mesh to obtain catalyst B. In the presence of catalyst B, a starting gas composed of 90% by volume of ammonia and 10% by volume of ethylenimine was passed at a space velocity of 5,000 hr$^{-1}$ (STP) and reacted at 360° C. The results are shown in Table 1.

EXAMPLE 17

Using the catalyst B prepared in Example 16, a starting gas composed of 70% by volume of ammonia, 10% by volume of ethylenimine and 20% by volume of nitrogen was passed at a sapece velocity of 1,000 hr$^{-1}$ (STP) and reacted at 250° C. The results are shown in Table 1.

EXAMPLE 18

Using the catalyst B prepared in Example 16, a starting gas composed of 85% by volume of ammonia and 15% by volume of ethylenimine was passed at a space velocity of 1,000 hr$^{-1}$ (STP) under a pressure of 270 mmHg and reacted at 300° C. The results are shown in Table 1.

EXAMPLE 19

A 1N aqueous solution of calcium nitrate was added to Na-Y type zeolite, and the mixture was stirred at 80° C. for 24 hours. The supernatant liquid was removed by decantation, and a fresh supply of a 1N aqueous calcium nitrate solution was added. This operation was repeated twice. The product was fully washed with water, and then filtered and dried to obtain a Na-Y type zeolite ion-exchanged with Ca. From the atomic absorptiometry of the supernatant liquid, the filtrate and the washing combined, and the fluorescent X-ray analysis of the resulting Na-Y type zeolite, the Ca ion exchange ratio was 63%.

Ten grams of the resulting Na-Y type zeolite (Ca ion exchange ratio 63%) was compression-molded, dried in air at 120° C., calcined at 450° C. for 2 hours and pulverized to a size of 9 to 16 mesh to obtain catalyst B.

Using the resulting catalyst B, a starting gas composed of 95% by volume of ammonia and 5% by volume of ethylenimine was passed at a space velocity of 6,000 hr$^{-1}$ and reacted at 340° C. The results are shown in Table 1.

EXAMPLE 20

Na-mordenite (La ion exchange ratio 85%) ion-exchanged with La was prepared by the same procedure as in Example 19 except that Na-mordenite was used instead of the Na-Y type zeolite and an aqueous solution of lanthanum nitrate was used instead of the 1N aqueous calcium nitrate solution. Ten grams of this product was compression-molded, dried in air at 120° C., calcined at 500° C. for 2 hours, and pulverized to a size of 9 to 16 mesh to obtain catalyst B.

In the presence of catalyst B, a starting gas composed of 90% by volume of ammonia, 5% by volume of ethylenimine and 5% by volume of nitrogen was passed at a space velocity of 3,000 hr$^{-1}$ (STP), and reacted at 320° C. The results are shown in Table 1.

EXAMPLE 21

H-mordenite (Fe ion exchange ratio 50%) ion-exchanged with Fe was prepared by the same procedure as in Example 19 except that H-mordenite was used instead of The Na-Y type zeolite and an aqueous solution of iron nitrate was used instead of the 1N aqueous calcium nitrate solution. Ten grams of this produce was compression-molded, dried in air at 120° C., calcined at 500° C. for 2 hours, and pulverized to a size of 9 to 16 mesh to obtain catalyst B.

In the presence of catalyst B, a starting gas composed of 80% by volume of ammonia and 20% by volume of ethylenimine passed at a space velocity of 2,000 hr$^{-1}$ (STP), and reached at 340° C. The results are shown in Table 1.

EXAMPLE 22

H-mordenite (Cu ion exchange ratio 10%) ion-exchanged with Cu was prepared by the same procedure as in Example 19 except that H-mordenite was used instead of the Na-Y type zeolite and an aqueous solution of copper nitrate was used instead of the 1N aqueous calcium nitrate solution. Ten grams of this product was compression-molded, dried in air at 120° C., calcined at 450° C. for 2 hours, and pulverized to a size of 9 to 16 mesh to obtain catalyst B.

In the presence of catalyst B, a starting gas composed of 85% by volume of ammonia and 15% by volume of ethylenimine passed at a space velocity of 3,000 hr$^{-1}$ (STP), and reacted at 380° C. The results are shown in Table 1.

EXAMPLE 23

H-mordenite (Pd ion exchange ratio 10%) ion-exchanged with Pd was prepared by the same procedure as in Example 19 except that H-mordenite was used instead of the Na-Y type zeolite and an aqueous solution of [Pd(NH$_3$)$_4$]Cl$_2$ was used instead of the 1N aqueous calcium nitrate solution. Ten grams of this product was compression-molded, dried in air at 120° C., calcined at 400° C. for 2 hours, and pulverized to a size of 9 to 16 mesh to obtain catalyst B.

In the presence of catalyst B, a starting gas composed of 70% by volume of ammonia, 10% by volume of ethylenimine and 20% by volume of nitrogen was passed at a space velocity of 1,500 hr$^{-1}$ (STP), and reacted at 270° C. The results are shown in Table 1.

TABLE 1

| Example | Catalyst | Reaction material | Space velocity (hr$^{-1}$) | Reaction temperature (°C.) | NH$_3$/aziridine compound/nitrogen (vol. %) | Conversion of the aziridine compound | Ethylenediamine Selectivity (mole %) | Ethylenediamine One-pass yield (mole %) |
|---|---|---|---|---|---|---|---|---|
| 1 | Al$_2$O$_3$ | ethylenimine | 3000 | 300 | 95/5/0 | 73.1 | 18.2 | 13.3 |
| 2 | ZrO$_2$ | propylenimine | 4000 | 380 | 95/5/0 | 42.6 | 21.2 | 9.0 |
| 3 | Nb$_2$O$_5$ | ethylenimine | 3000 | 300 | 90/10/0 | 19.6 | 62.4 | 12.2 |
| 4 | WO$_3$/SiO$_2$ | 2-ethylethylenimine | 3000 | 350 | 90/10/0 | 33.3 | 22.1 | 7.4 |
| 5 | AlPO$_4$ | ethylenimine | 5000 | 380 | 80/20/0 | 82.3 | 31.9 | 26.3 |
| 6 | AlPO$_4$ | ethylenimine | 4000 | 370 | 10/10/80 | 74.6 | 25.4 | 18.9 |
| 7 | BPO$_4$ | propylenimine | 4000 | 350 | 5/5/90 | 62.8 | 22.7 | 14.3 |
| 8 | KH$_2$PO$_4$/SiO$_2$ | ethylenimine | 4000 | 400 | 80/20/0 | 48.6 | 28.3 | 13.8 |
| 9 | KH$_2$PO$_4$/SiO$_2$ | ethylenimine | 2500 | 380 | 50/50/0 | 44.5 | 20.0 | 8.9 |
| 10 | Cs$_2$SO$_4$/SiO$_2$ | 2-ethylethylenimine | 7000 | 450 | 50/5/45 | 32.6 | 21.9 | 7.1 |
| 11 | Na$_2$WO$_4$/SiO$_2$ | propylenimine | 5000 | 390 | 50/5/45 | 41.6 | 26.3 | 10.9 |
| 12 | kaolin | ethylenimine | 6000 | 400 | 80/20/0 | 72.6 | 55.8 | 40.5 |
| 13 | kaolin | ethylenimine | 500 | 120 | 80/20/0 | 22.1 | 66.2 | 14.6 |
| 14 | montmorillonite | ethylenimine | 4000 | 300 | 80/20/0 | 46.2 | 65.3 | 30.2 |
| 15 | ZSM-5 | ethylenimine | 9000 | 430 | 90/10/0 | 44.6 | 54.7 | 24.4 |
| 16 | H-mordenite | ethylenimine | 5000 | 360 | 90/10/0 | 63.9 | 70.2 | 44.9 |
| 17 | H-mordenite | ethylenimine | 1000 | 250 | 70/10/20 | 52.9 | 83.2 | 44.0 |
| 18 | H-mordenite | ethylenimine | 1000 | 300 | 85/15/0 | 56.4 | 76.5 | 43.1 |
| 19 | Na-Y type zeolite (63% Ca) | ethylenimine | 6000 | 340 | 95/5/0 | 45.9 | 67.2 | 30.8 |
| 20 | Na-mordenite (85% La) | ethylenimine | 3000 | 320 | 90/5/5 | 55.7 | 77.3 | 43.1 |
| 21 | H-mordenite (50% Fe) | ethylenimine | 2000 | 340 | 80/20/0 | 54.5 | 84.6 | 46.1 |
| 22 | H-mordenite (61% Cu) | ethylenimine | 3000 | 380 | 85/15/0 | 57.8 | 80.1 | 46.3 |
| 23 | H-mordenite (10% Pd) | ethylenimine | 1500 | 270 | 70/10/20 | 54.1 | 84.9 | 45.9 |

EXAMPLE 24

Calcium hydroxide (2.22 kg) and 120 g of sodium hydroxide were suspended in 10 liters of pure water, and 1.73 kg of 85% by weight orthophosphoric acid was added. The mixture was heated with sufficient stirring. The concentrate was evaporated to dryness, and further dried in air at 120° C. for 12 hours. The product was pulverized, kneaded fully with a small amount of water, the kneaded mixture was molded into a ring shape having an outside diameter of 6 mm, a length of 6 mm and an inside diameter of 2 mm, dried in air at 200° C. for 12 hours, and calcined at 700° C. for 5 hours to give a catalyst A having the composition of $Ca_1P_{0.5}Na_{0.1}$ by atomic ratios.

Zeolon (registered trademark) 900H E type (diameter 1/9 inch) made by Norton Co., U.S.A. which is a proton exchanged mordenite was used as a catalyst B.

One liter of catalyst A and 0.35 liter of catalyst B were filled in the stacked state in a stainless steel reaction tube having an inside diameter of 30 mm with the catalyst A on top, and then heated at 400° C. with a heat medium. A starting gas composed of 5% by volume of monoethanolamine and 95% by volume of ammonia was passed through the reaction tube at a space velocity of 3,500 $hr^{-1}$ for the catalyst A layer and 10,000 $hr^{-1}$ for the catalyst B layer and continuously reacted. The reaction conditions and the results of gas chromatographic analysis of the reaction product after 24 hours from the initiation of the reaction are shown in Table 2.

EXAMPLE 25

Catalyst A was prepared as in Example 24 except that its shape was changed to a pellet having a diameter of 4 mm and a length of 6 mm. One liter of the catalyst A and 0.35 liter of the catalyst B used in Example 24 were mixed, and filled in a stainless steel reaction tube having a n inside diameter of 30 mm. The temperature of the heat medium for the reactor was prescribed at 380° C. A starting gas composed of 10% by volume of monoethanolamine and 90% by volume of ammonia was passed through the tube and continuously reacted. The reaction conditions and the results are shown in Table 2.

EXAMPLE 26

One liter of catalyst A used in Example 24 and 0.35 liter of catalyst B used in Example 24 were filled in stainless steel reaction tubes having an inside diameter of 30 mm set up respectively in separate reactors, and the outlet of the reactor filled with catalyst A was connected to the inlet of the reactor equipped with catalyst B. The temperature of the heat medium for the reactor filled with catalyst A was preset at 410° C., and the temperature of the heat medium for the reactor filled with catalyst B, at 380° C. A starting gas composed of 20% by volume of monoethanolamine and 80% by volume of ammonia was passed through the reactors and continuously reacted. The reaction conditions and the results are shown in Table 2.

EXAMPLE 27

By using the same catalysts as in Example 24, the reaction was carried out by using the apparatus shown in the flowsheet of FIG. 1.

Catalyst A (1.06 liters) was filled in a stainless steel reaction tube (102), and heated at 400° C. with a heat medium. Monoethanolamine was fed from a feed line (1) to an evaporator (101), and the monoethanolamine vapor was passed through the reaction tube under a pressure of 80 mmHg at a space velocity of 200 $hr^{-1}$ and continuously reacted. The product gas was cooled to −10° C. with a condenser (103) and collected, and introduced into a distillation column (104) consisting of a stainless steel tube having an inside diameter of 50 mm and a height of 200 mm at a site about 1/3 of its height from the top. In the inside of the column, packings with a diameter of 6.35 mm (Mcmahon) were filled at a layer height of 400 mm in the concentrating portion and at a layer height of 1200 mm in the recovering portion. The operating pressure was 400 mmHg, and the reflux ratio was 4. From the top of the column, ethylenimine in a concentration of 99.1% by weight was obtained in an amount of 195 g per hour. The resulting ethylenimine was fed into an evaporator (105) via a line (2) and mixed with an ammonia gas from a line (3) to prepare a starting gas containing 5% by volume of ethylenimine. A stainless steel reaction tube (106) having an inside diameter of 30 mm and filled with 0.338 liter of catalyst B was heated at 320° C. with a heat medium. The starting gas was passed through the reaction tube at a space velocity of 6,000 $hr^{-1}$. The reaction conditions and the results of gas-chromatographic analysis of the reaction product sampled 24 hours after the initiation of the reaction are shown in Table 3.

EXAMPLE 28

A reaction was carried out by suing the same catalysts as in Example 24 and the appparatus shown in the flowsheet of FIG. 2.

Catalyst A (1.06 liters) was filled in a stainless steel reaction tube (202) having an inside diameter of 30 mm and heated at 400° C. with a heat medium. Monoethanolamine was fed into an evaporator (201) from a feed line (21), and the monoethanolamine vapor was diluted with nitrogen gas from a line (22) to prepare a starting gas containing 20% by volume of monoethanolamine. The starting gas was passed through the reaction tube at a space velocity of 1,000 $hr^{-1}$ and continuously reacted. The product gas was cooled to 100° C. with a condenser (203) and introduced into the bottom portion of a collector column (204) having an inside diameter of 200 mm and a height of 2,000 mm and filled with packings having a diameter of 6.35 mm (Mcmahon). Monoethanolamine as a collected liquid was fed at a rate of 4 kg/hr from the top of the column via a feed line (23). The collected liquid withdrawn from the bottom of the column was introduced into a distillation column (205) consisting of a stainless steel tube having an inside diameter of 50 mm and a height of 200 mm at a site about ⅓ of its height from the top. In the inside of the column, packings having a diameter of 6.35 mm (Mcmahon) were filled in a layer height of 400 mm in the concentrating portion and at a layer height of 1,200 mm in the recovering portion. The operating pressure was 400 mmHg, and the reflux ratio was 4. From the top of the distillation column, 192 g/hr of ethylenimine in a concentration of 98.9% by weight was obtained. The resulting ethylenimine was fed into an evaporator (206) via a feed line (24) and mixed with ammonia gas from a feed line (25) to prepare a starting gas containing 20% by volume of ethylenimine. A stainless steel reaction tube (207) filled with 0.5 liter of catalyst B was heated at 350° C. with a heat medium, and the starting gas was passed through the reaction tube at a space velocity of 4,000 $hr^{-1}$. The reaction conditions and the results of gas-chromatographic analysis of the reaction product 24 hours from the initiation of the reaction are shown in Table 3.

EXAMPLE 29

Cesium nitrate (350 g), 8 g of sodium hydroxide and 184 g of 85% phosphoric acid were dissolved in 6 liters of deionized water, and as a carrier, 1.2 kg of silica gel was added. Furthermore, 7.6 g of aluminum nitrate was added, and the mixture was concentrated by heating. The concentrate was dried at 120° C. for 12 hours, then pulverized, fully kneaded with a small amount of water, and molded into pellets each having a diameter of 5 mm and a length of 5 mm. The pellets were dried in air at 200° C. for 12 hours and then calcined at 700° C. for 4 hours to give catalyst A having the composition $Cs_{0.9}Na_{0.1}P_{0.8}Al_{0.01}$ by atomic ratios.

Acid clay (1 kg) was mixed with a small amount of water and molded into pellets each having an outside diameter of 5 mm and a length of 5 mm. The pellets were dried in air at 120° C. for 12 hours, and then calcined at 500° C. for 5 hours to give catalyst B.

By suing catalysts A and B, the same reaction as in Example 24 was repeated. The reaction conditions and the results are shown in Table 2.

TABLE 2

| Example | Reaction temperature (°C.) (A) | (B) | Space velocity (hr$^{-1}$) (A) | (B) | Monoethanolamine Concentration (vol. %) | Conversion (mole %) | Ethylenimine selectivity (mole %) | Ethylenediamine Selectivity (mole %) | One-pass yield (mole %) |
|---|---|---|---|---|---|---|---|---|---|
| 24 | 400 | | 3,500 | 10,000 | 5 | 85.6 | 31.3 | 55.1 | 47.2 |
| 25 | 380 | | | 2592 | 10 | 73.2 | 34.4 | 52.2 | 38.2 |
| 26 | 420 | 380 | 3,500 | 10,000 | 20 | 82.9 | 39.1 | 51.1 | 42.4 |
| 29 | 360 | | 4,000 | 8,000 | 2 | 95.1 | 41.2 | 38.9 | 37.0 |

TABLE 3

| Example | Reaction temperature (°C.) (A) | (B) | Space velocity (hr$^{-1}$) (A) | (B) | Concentration of monoethanolamine (vol. %) | Ethylenimine Concentration (vol. %) | Conversion (mole %) | Ethylenediamine Selectivity (mole %) | One-pass yield (mole %) |
|---|---|---|---|---|---|---|---|---|---|
| 27 | 400 | 360 | 200 | 5,000 | 100 | 5 | 70.0 | 75.2 | 52.6 |
| 28 | 400 | 350 | 200 | 4,000 | 100 | 20 | 45.8 | 75.4 | 34.5 |

EXAMPLE 30

Example 24 was repeated except that a starting gas composed of 10% by volume of isopropanolamine and 90% by volume of ammonia was used. The results were as follows:

Isopropanolamine concentration: 10% by volume
Isopropanolamine conversion: 78.4 mole %
2-Methylethylenimine selectivity: 33.2 mole
Methylethylenediamine selectivity: 51.7 mole %
Methylethylenediamine one-pass yield: 40.5 mole %

We claim:

1. A method of producing ethylenediamines represented by the general formula

  (I)

wherein R represents a hydrogen atom, or a methyl or ethyl group, which comprises reacting at a temperature of 100 to 500° C. an aziridine compound of the general formula

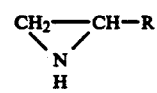  (II)

wherein R is as defined, with ammonia in the gaseous phase in the presence of a solid acid catalyst.

2. The method of claim 1 in which the mole ratio of ammonia to the aziridine compound is at least 1.

3. The method of claim 1 in which the solid acid catalyst is a molecular sieve-type catalyst.

4. The method of claim 2 in which the mole ratio of ammonia to the aziridine compound is from 1 to 50.

5. The method of claim 1 in which the reaction is carried out at a temperature of 200 to 450° C.

6. The method of claim 1 in which the solid acid catalyst is an oxide selected from the group consisting of silicon oxide, zirconium oxide, titanium oxide, aluminum oxide, zinc oxide, cadmium oxide, lead oxide, bismuth oxide, niobium oxide, lanthanum oxide, antimony oxide and yttrium oxide.

7. The method of claim 1 in which the solid acid catalyst is a clay mineral selected from the group consisting of kaolin, bentonite and montmorillonite.

8. The method of claim 1 in which the solid acid catalyst is an oxo acid salt selected from the group consisting of phosphates, borates, sulfates, niobates, tungstates, molybdates and titanates.

9. The method of claim 1 in which the space velocity is 100 to 30,000 hr$^{-1}$.

10. The method of claim 1 in which the space velocity is 500 to 10,000 hr$^{-1}$.

* * * * *